US007032467B2

(12) United States Patent
Yoon

(10) Patent No.: US 7,032,467 B2
(45) Date of Patent: Apr. 25, 2006

(54) PACKAGE BIOCHEMICAL HAZARD AND CONTRABAND DETECTOR

(76) Inventor: Sung Hoon Yoon, 218 Broad Ave. Apt. 3C, Leonia, NJ (US) 07605

( * ) Notice: Subject to any disclaimer, the term of this patent is extended or adjusted under 35 U.S.C. 154(b) by 0 days.

(21) Appl. No.: 10/281,680

(22) Filed: Oct. 28, 2002

(65) Prior Publication Data

US 2003/0136203 A1 Jul. 24, 2003

Related U.S. Application Data

(60) Provisional application No. 60/344,635, filed on Oct. 26, 2001.

(51) Int. Cl.
*G01N 1/38* (2006.01)

(52) U.S. Cl. .................. 73/863.81; 73/23.2; 73/31.03; 73/31.04; 73/31.07

(58) Field of Classification Search ............ 73/864.33, 73/31.03, 863.22, 23.2, 24.01, 24.06, 31.07, 73/863.81; 340/540, 5.3; 209/143
See application file for complete search history.

(56) References Cited

U.S. PATENT DOCUMENTS

| | | | | |
|---|---|---|---|---|
| 4,580,440 | A * | 4/1986 | Reid et al. | 73/31.07 |
| 4,718,268 | A * | 1/1988 | Reid et al. | 73/19.01 |
| 5,795,544 | A * | 8/1998 | Matz | 422/83 |
| 5,942,699 | A * | 8/1999 | Ornath et al. | 73/863.21 |
| 6,613,571 | B1 * | 9/2003 | Cordery et al. | 436/48 |
| 2001/0029793 | A1 * | 10/2001 | Moler et al. | 73/863.22 |
| 2002/0124664 | A1 * | 9/2002 | Call et al. | 73/863.22 |
| 2002/0126008 | A1 * | 9/2002 | Lopez et al. | 340/540 |
| 2002/0157993 | A1 * | 10/2002 | Call et al. | 209/143 |
| 2003/0034874 | A1 * | 2/2003 | Mann | 340/5.3 |
| 2003/0058099 | A1 * | 3/2003 | Lopez et al. | 340/540 |
| 2003/0075592 | A1 | 4/2003 | Fuisz | |
| 2003/0082073 | A1 | 5/2003 | Mankovitz | |
| 2003/0085348 | A1 * | 5/2003 | Megerle | 250/287 |
| 2003/0106929 | A1 | 6/2003 | Day | |
| 2003/0108981 | A1 | 6/2003 | Robinson | |
| 2003/0113230 | A1 | 6/2003 | Cordery | 422/68.1 |
| 2003/0113922 | A1 | 6/2003 | Cordery | 436/1 |
| 2003/0114957 | A1 | 6/2003 | Cordery | 700/228 |
| 2003/0119175 | A1 | 6/2003 | Stradley | 435/287.1 |
| 2003/0124039 | A1 | 7/2003 | Ryan, Jr. | |
| 2003/0125835 | A1 | 7/2003 | William | |
| 2003/0133539 | A1 | 7/2003 | Haas | |
| 2003/0136920 | A1 | 7/2003 | Flores et al. | |
| 2003/0138344 | A1 | 7/2003 | Mielnik et al. | |
| 2003/0140015 | A1 | 7/2003 | Applebaum | |
| 2003/0144800 | A1 | 7/2003 | Davis et al. | |
| 2003/0145664 | A1 | 8/2003 | Schwarz et al. | 73/863.22 |
| 2003/0159916 | A1 | 8/2003 | Chen | |

* cited by examiner

*Primary Examiner*—Daniel S. Larkin
(74) *Attorney, Agent, or Firm*—Law Offices of Rita C. Chipperson, P.C.; Rita C. Chipperson

(57) ABSTRACT

This apparatus and method allows collection concentrated sample of content in shipping packages without unsealing the package by forcing airflow via existing hidden gaps or, if necessary, creating one by a small incision. The air is injected into the hidden gaps by either probe or socket device to disturb and agitate contents inside the package, causing the contents to loosen and blend particulates on the surface into the air stream. Airborne particles are channeled into detection device, where the particulates are concentrated. Display and warning apparatus receives and records the analysis results from detection device. If the analysis finds that predetermined selection and sensitivity criteria for target hazard or contraband is met, then the warning apparatus initiates appropriate alert protocols.

8 Claims, 4 Drawing Sheets

PACKAGE BIOCHEMICAL HAZARD AND CONTRABAND DETECTOR

CROSS REFERENCE TO RELATED APPLICATIONS

This application claims the benefit filing date of Provisional Patent Application Ser. No. 60/344,635, filed on Oct. 26, 2001.

BACKGROUND OF THE INVENTION

The following relates to an apparatus and method to detect hazardous or illegal contraband hidden within shipping, delivery, mail, or postal packages for analysis and defense without fully unsealing the packages by probing the interior with airflow and collecting concentrated sample particles.

According to US Department of Justice guide (NIJ Guide 101-00), most of the well known biological weapon agents such as, anthrax, Brucellosis, Tularemia, Cholera, Glanders, Melioidosis, Plague, Marburg Virus, Smallpox Virus, Venezuelan Equine Encephalitis, Ebola Virus, Q Fever, Botulinum Toxin, Staphylococcal enterotoxin B, Tricothecene mycotoxins, and Ricin could take aerosol form. The agency further states, "The primary infection route from exposure to biological agents is through inhalation."

During the year 2001, envelopes containing anthrax spores were sent via the US Postal Service. The cutaneous form of anthrax spores caused havoc as it infected people who came in direct contact with the hazardous powder. However, the inhalation form of anthrax spores caused even greater fear and devastation, as the fine airborne spores randomly contaminated nearby packages and killed indiscriminately and capriciously. Moreover, the inhalation form was much deadlier than the cutaneous form, as many died even with antibiotic treatments.

Soon afterward, the fear of other biological agents and envelopes containing non-toxic materials preyed on the fear. Although no one suffered illness or death, the "hoax-envelopes" flood was nearly as effective in terrorizing the public and consuming valuable resources as the real biological attacks, since every incident had to be treated like the real thing.

In response, the US Government irradiated mail packages bound for various government agencies and certain targeted private sectors. Even after a three billion dollars budget was allotted and nearly a year had past since the incidents, the majority of the mail packages sent to the general public have yet to be irradiated or otherwise protected.

Some reasons for this are that the irradiation is an expensive process, it takes a long time to implement, and it alone cannot pinpoint the contaminated or hoax mail. Additionally, the possibility of infection among those unfortunate postal workers prior to irradiation at a central processing unit can be tragic. Also, the irradiated mail may cause health problems for the recipients. Many congressional workers had complained of headache, nose bleeding, diarrhea, and other ailments. As a result, many members of the public oppose and fear the irradiation process.

The irradiated mail must be stored for several days to lower the level of radiation, which delays delivery and incurs storage cost. No clear procedure exists to avoid irradiation products that can be damaging, destructive, or even more harmful if they are exposed to massive doses of radiation, such as electronic devices, film, glass, and food items.

Exposing metal to ionizing radiation can induce radioactivity if enough of it collects on the surfaces. There's a lot of metal in the mailroom in the form of binders, paperclips, and pens, not to mention all of the consumer products containing metal that are routinely shipped via the U.S. Postal Service that could cause such an exposure. Additionally, the irradiation needs nuclear materials to keep it operating. Transporting radioactive material, improper worker safety, and environmental contamination from leaks, spills, or other mishaps can lead to disasters. Yet another concern is that a terrorist may attack the irradiation facility, transport, or storage to obtain the irradiated material to create a "dirty bomb."

In summary, the effectiveness of the process may be exaggerated. A New Jersey official described some of the challenges in a memo. "After much discussion about the penetration of the electron beam," she wrote, "it was determined that the package would have to be turned over and run through irradiator a second time. The problem is that the spores in the envelopes would presumably fall to the bottom by gravity, thus avoiding the beam for both passes."

Another patent pending idea by Gary Mize called "Biosafe Mailbox" uses time released toxins like chlorine dioxide or methyl bromide in a mailbox prior to pick up. This idea also suffers many of the problems associated with irradiation. The toxins that are used to destroy the biological agents are dangerous chemicals themselves, are probably only effective against a limited few biological agents, and are ineffective against chemical toxic agents. Moreover, reconfiguring every mailbox to release and recycle these chemicals could be not only very expensive, but also potentially harmful, as toxins may be released to the environment. Not to mention that these processes can be thwarted easily, using lead foils to block the irradiation and airtight package can stop the decontaminants.

The danger to the public using delivery service, however, is not new. Long before the biochemical terrorism, illegal contrabands such as bombs, poisons, illegal drugs, and the like have been sent using US Postal mail.

Available technologies like Ion Mobility Spectrometry (IMS), vapor detection, gas chromatograph, reactive chemicals, or similar processes have had only limited use for detecting hazards and contraband inside delivery packages, because collecting concentrated content samples from a sealed container proves to be difficult.

X-ray and swab collection method, often used in airports, would be ineffective, too costly, and time consuming to use for delivery services due to high volumes. Tens of millions of letters and packages that are sent by delivery services per day cannot be individually viewed and swabbed.

A better sample collection and concentration apparatus and method must be utilized, if advanced analytic technologies are to be implemented.

SUMMARY OF THE INVENTION

Whether it is real or a hoax, the best defense against bio-terrorists or other criminal activities, is catching and prosecuting the perpetrator. To catch the offenders, law enforcement must be able to identify the crime quickly and secure the evidence without destroying or altering it. As selection, detection, and identification technologies improve, such as nucleic acid amplification or antibody binding method, obtaining enough concentrated sample, quickly cueing the existence of the possible target agents inside the package, and preserving the evidence becomes critical.

The idea described herein is an inexpensive and an effective apparatus and method to collect concentrated possible biochemical hazard and other illegal contrabands samples in packages for analysis. Given that the envelope has been the choice of a delivery vehicle by the terrorists and many other illegal activities, an envelope will be used as an example, although other shipping packages can also utilize similar apparatuses and methods.

Most shipping or mail packages are semi-sealed and have gaps or openings where packaging material edges meet. This is to prevent air from being trapped inside the package and turning it into a balloon, because a ballooned envelope takes up excess space and causes problems when transporting. Shipping or mailing packages usually do not contain particles that resemble the size and weight of biological pathogens or chemical toxins and bombs and illegal drugs exhibit specific particle characteristic signatures. The possible harmful particles in the package are of such size and weight that they should become airborne and mobile by introducing air or gas flow via the gap.

In summary, the process results in the following objectives and advantages: provides a cheap and effective apparatus to thwart biochemical terrorism rather than using expensive and dangerous ultraviolet sterilization method, slow x-ray process, or expensive new mailboxes without unsealing the package, provides safe and easy operation, as the process does not require dangerous radiation or chemicals, provides a method to help quickly apprehend criminals and reduce exposure because the method could detect the presence of foreign particles early and stop it from going to the addressee or another transfer agent, provides defense against hoax biological terror attacks, provides better and concentrated sample collection, and provides additional testing for many illegal contrabands like illegal drugs and bombs.

In accordance with the present invention, is a simple, safe, and effective concentrated sample collection and cueing apparatus and method against biochemical hazard and illegal contrabands without fully unsealing shipping, delivery, mail, or postal packages.

Further objects and advantages will become apparent from a consideration of the drawing and ensuing description.

REFERENCE NUMERALS IN DRAWINGS

Figure 1:
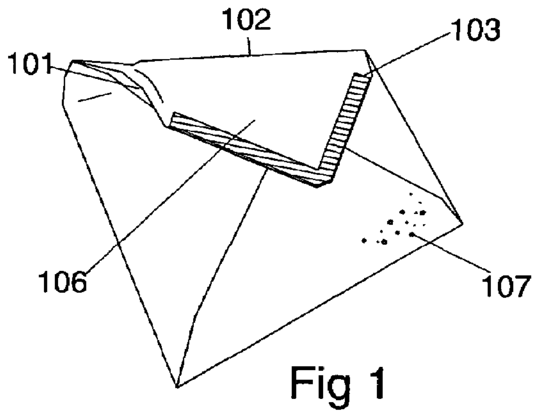
FIG. 1 depicts a standard sealed US envelope with a small gap or opening highlighted.

101. Hidden gap or opening in mailing package
102. Envelope
103. Envelope adhesive area
105. Express Mail shipping package
106. Envelope Flap
107. Possible biochemical hazard material (inside the envelope)
108. Side compressor clamp pairs connected to sensors for checking inflation of the envelope
109. Airtight container or box in this embodiment
110. Airtight box door
111. Conveyer system (to deliver the envelope to the box)
112. Mechanical clamp pairs (to hold the envelope in place)
114. Mechanical probe
114A. Strait probe
114B. Narrow probe
114C. Bent Probe
114D. Slanted Probe
114E. Hollow channel running down the middle on the probe
115. Probe control box
116. Probe movements from rest to under the envelope flap
117. Side clamp movements (coming together to squeeze the envelope)
118. Tube to pump air or gas into the envelope
119. Tube for vacuum out the air or gas
122. Inflation or ballooning of envelope sidewalls by air
123. A rod guide for the probe control box movement
124. Lowering motion of the control box along the rod guide
125. Axis to turn the box
126. The airtight box rotating around the axis
130. Mechanical scissor (cutting motion)
131. Syringe like device (punching a hole)
133. Forced movement of air or gas
134. Detection or Analytic device (for concentration and analysis of particulates)
135. Possible biochemical hazard material airborne
137. Display and warning apparatus
138. Socket lips device
139. Airflow into the envelope socket device above
139A. Residual airflow
140. Hole connected tube to force air into envelope via the socket device
141. Hole in the box with vacuum tube to collect sample particles
142. Airflow measurement device
143. Backward pressure on the clamp

DETAILED DESCRIPTION

Figure 2:
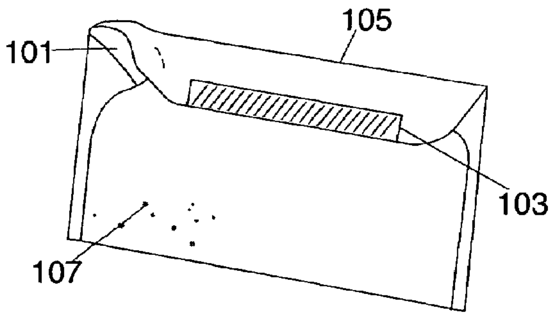
FIG. 2 depicts a sealed express mail package also with a gap highlighted.

As depicted in FIG. 1 and FIG. 2, the vast majority of envelopes or packages used in the US have small gaps or openings on the top corners where edges come together that can be probed without unsealing the subject. Opening 101 still exists even when flap 106 on envelope 102 or package 105 is closed and sealed.

In FIG. 2, an adhesive area 103 does not extend all the way out to the corner edge of the envelope. This creates the gap above, which exists to vent air in and out when being handled. Without it, the envelope will not flatten as trapped air creates ballooning, which will then cause problems as it travels through the processing plants. The small opening is well concealed and covered by the flap. This cover usually keeps possible hazardous and contraband particles 107 trapped inside the envelope.

Figure 3:
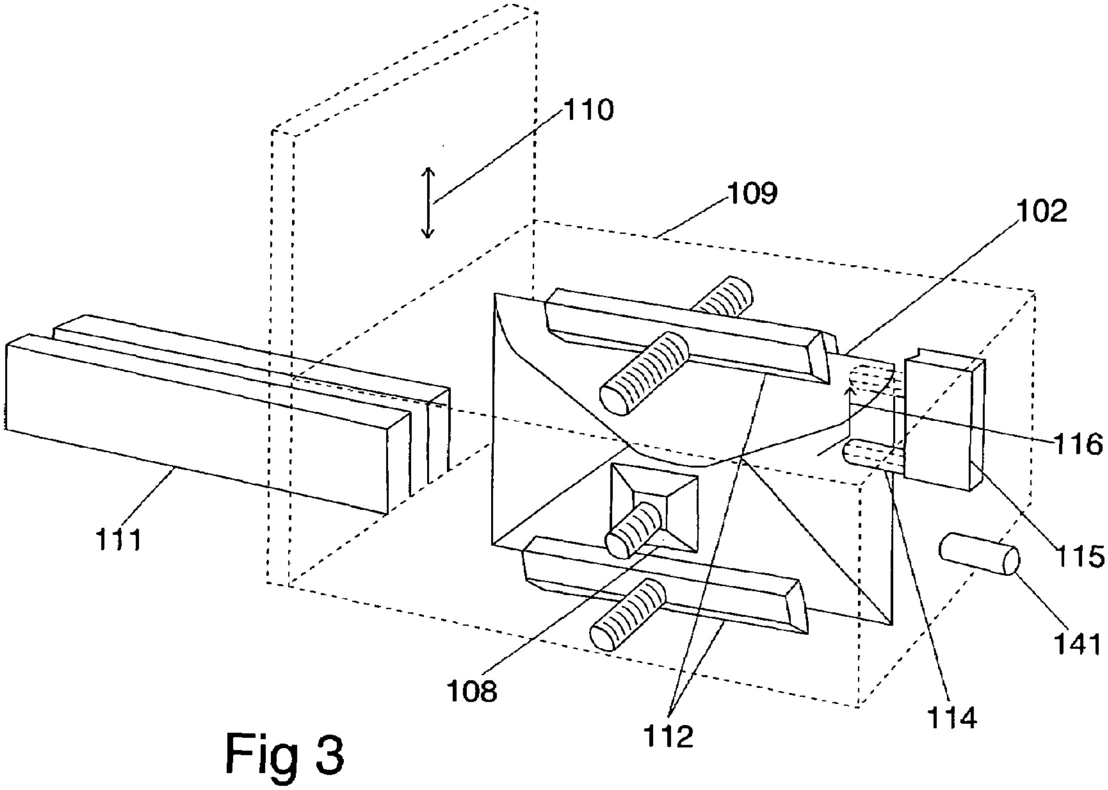
FIG. 3 depicts an airtight container with the above envelope inserted with clamps, sensors, and probe control box.

As shown in FIG. 3, envelope 102 travels by conveyer belt mechanism 111 or gloved human hands to an airtight container 109, which is a box in this embodiment. Once inside the airtight box, envelope 102 is secured by holding clamps 112 on an outer edge of the envelope sides. In this embodiment, top and bottom clamps are utilized. The envelope is locked in the box by closing airtight door 110. Once envelope 102 has been secured by the operations just described, move side compressor clamps 108 with optical or pressure sensors (not shown) close against the side walls of the envelope. Such that, when the envelope is inflated, the ballooning envelope sidewalls push back the side clamps. FIG. 3 also illustrates the probe attached to control box 115 at rest prior to exploring the gap. By using optical or mechanical sensors, mechanically slide small probe 114 under the envelope flap by following arrow movements 116. This operation is described in further detail below.

Figure 4:
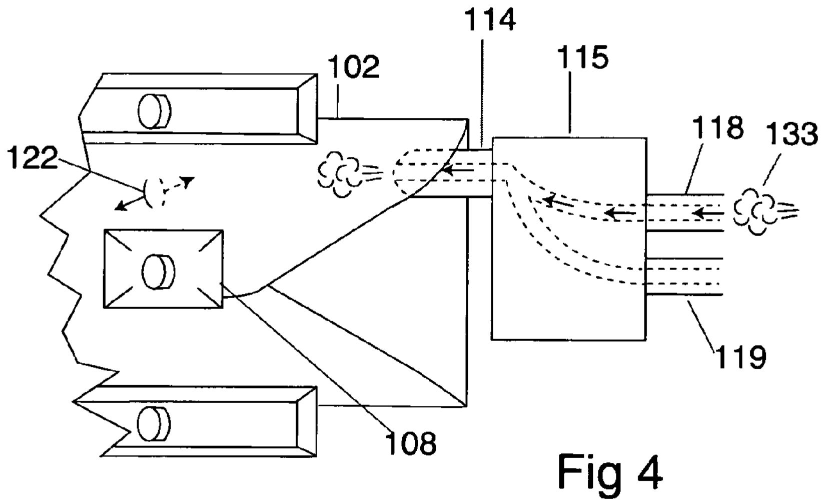
FIG. 4 depicts the right frontal right half view of the inserted and clamped secure envelope depicts FIG. 3.
Figure 8:
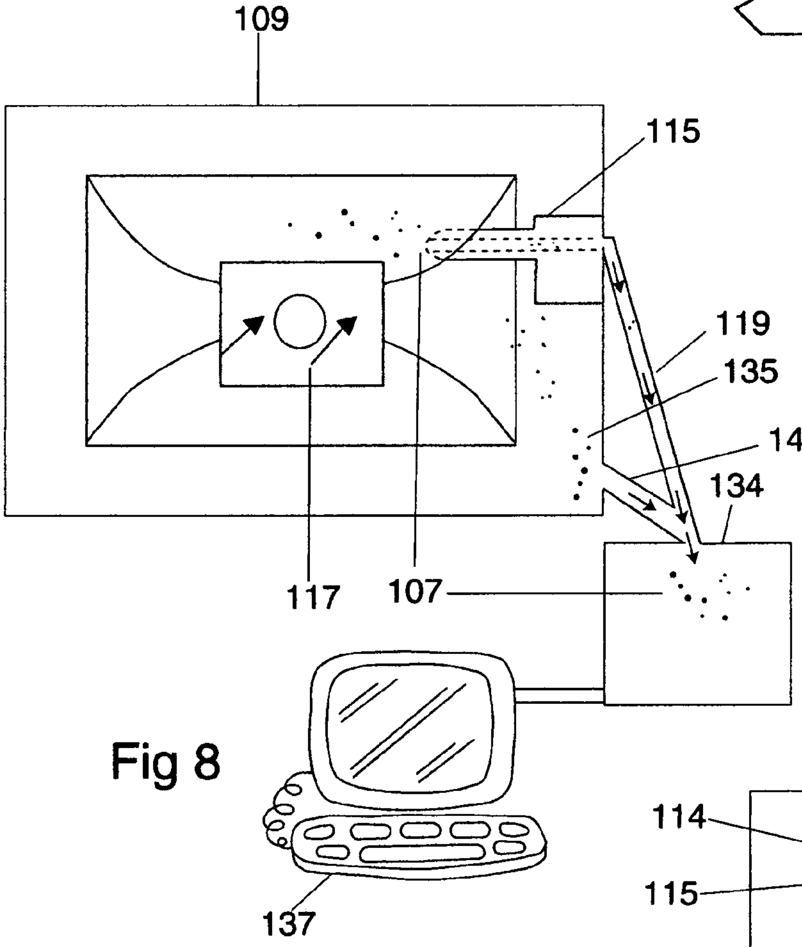
FIG. 8 depicts the airtight box in FIG. 3 attached to a detection device and then to a warning system.
Figure 8A:
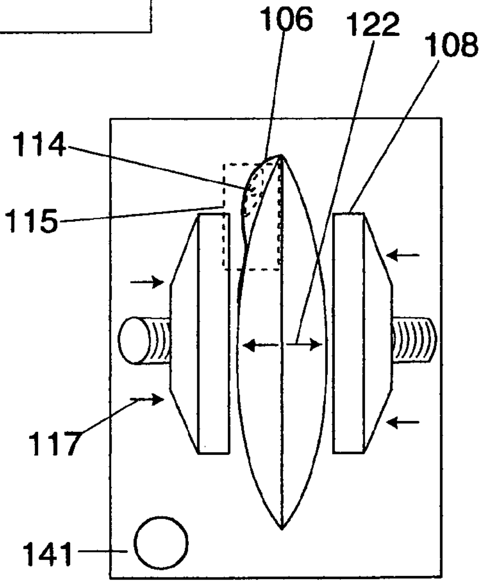
FIG. 8A depicts a side view of the airtight box with an inflated envelope in the middle of the side compressor clamp with sensors.

FIG. 4 shows the exposed front right half of the airtight box from FIG. 3 in detail with items inside mechanical control and sensor box 115 with attached the probe. The control box contains mechanical devices with sensors (not shown) to guide probe 114 underneath envelope flap 106. The exact mechanical and sensor devices to guide the probe into the gap are not included as part of the invention. The control box contains two air hoses inside. First hose 118 injects the air or gas to the probe tip and inflates 122 the envelope during the insertion process show in movement 116. Second hose 119 will be then used later for collecting a sample by vacuuming the air and particles inside the envelope after ballooning, as shown in FIGS. 8 and 8A.

Figure 4A:
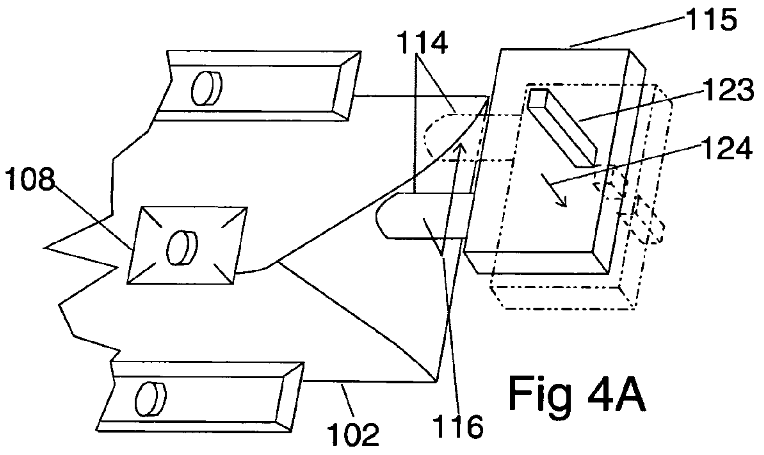
FIG. 4A depicts a perspective view of FIG. 4 to illustrate the probe and control box in more detail.

FIG. 4A shows a detailed perspective view of FIG. 4 with one embodiment of the probe and the to control box movement. The probe is attached to control box 115, which is attached to guiding rod 123. The control box apparatus is lowered and rested along guide rod 123 on top of the envelope and insert it under the flap by mechanically traveling along the side of the envelope. As the probe slides up and approaches the flap, the probe expels a constant air stream from its tip, to push the envelope wall and the flap further apart to enlarge the gap.

Figure 5:
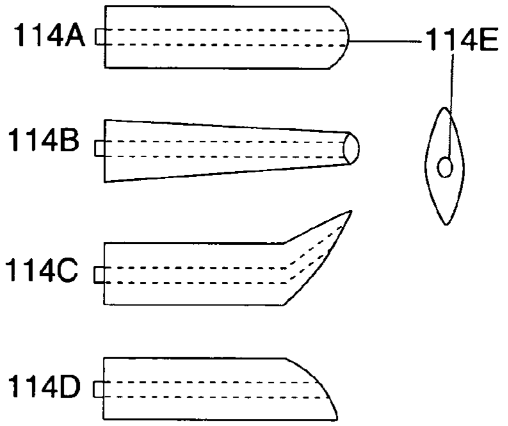
FIG. 5 depicts variations of probe shapes.

FIG. 5 is a closer look at variants of a probe. The probe shape can be varied like a straight tip 114A, a narrowed tip 114B, a bent tip 114C, or a slanted tip 114D. However, regardless of the exact shape or material, the probe is thin, dull, pointed, and hollow device that can easily be slipped in the gap. Materials of the probe can be metal, ceramic, plastic, or the like. The outer shape of the probe may resemble the end of a letter opener knife, but a hollowed middle channel 114E extends from the tip to the end, which enables the air or gas movement back and forth from control box 115.

Figure 6:
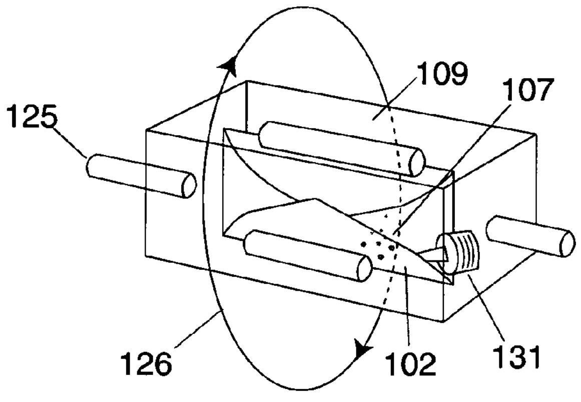
FIG. 6 depicts a bottom view the airtight box in FIG. 3.

FIG. 6 shows an optional embodiment of the airtight box in FIG. 3 inverted to show possible rotation of the whole box apparatus in FIG. 3. The whole airtight box may be mechanically rotated 126 over on axis 125 by turning on a motor (not shown) attached to the axis. As the box turns, gravity and centrifugal force will help to loosen the particles. Additionally, other motions like shaking or vibrating could achieve similar results. Perform this step on the probed and ballooned envelope.

Figure 7:
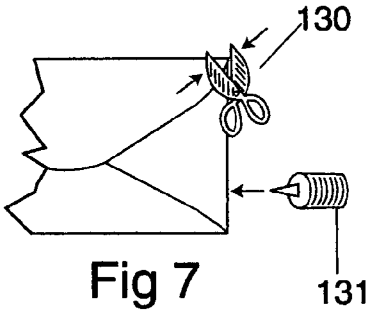
FIG. 7 depicts the envelope being infiltrated by a pair of scissors or a syringe.

If the envelope fails to balloon by flowing air from the probe tip, cut a small opening with a pair of scissors 130 or pokes a hole with a syringe 131 to create an opening that can be used to introduce air or gas inside the envelope, as seen in FIG. 7.

As in FIG. 8A, determine if the gas has successfully penetrated the interior of the envelope and expanded envelope sidewalls 112 by checking the pressure exerted against the side clamp 108. Afterward, force the envelope to deflate to induce the air/gas out of the envelope carrying the possible hazardous material by squeezing envelope-walls together 117 on both sides with the side clamps.

Turning to FIG. 8, collect the airborne biochemical hazard particles sample 135 via probe channel 114E using vacuum hose 119 and hole 141 in the box. Send the sample to detection device 134, which can be a laser analyzer, a photometer, an optical particle counter (OPC), a condensation particle counter (CPC), an optoelectronic sensor, or other particle, optical, biological, or chemical analysis method.

Afterward, display unit 137 shows analyzed and stored results. The unit can be a combination of computer or electronic devices. The exact technical specification of the unit is not part of the invention. If certain selection and sensitivity criteria is reached in any one or more of criteria, like particle count, particle mass, particle density, particle concentration, chemical reaction, generic response, or the like, then an alarm alerts the operator by sound, flashing screen, e-mail, and/or other communication methods.

Figure 9:
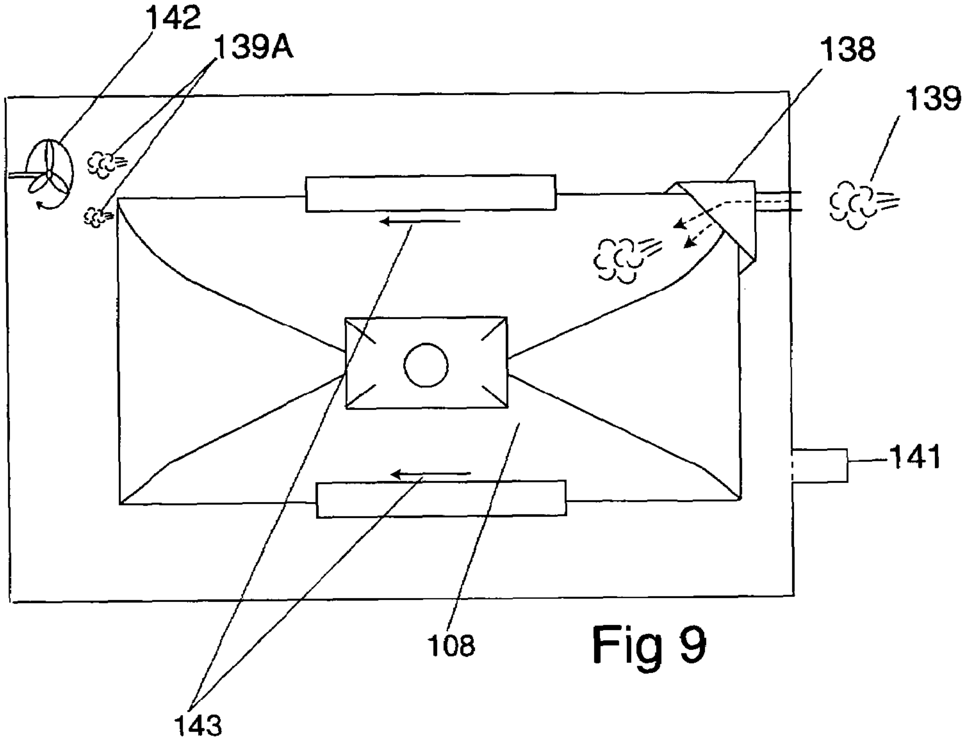
FIG. 9 depicts a frontal view with a socket lip device variant to the probe used in FIG. 4.
Figure 9A:
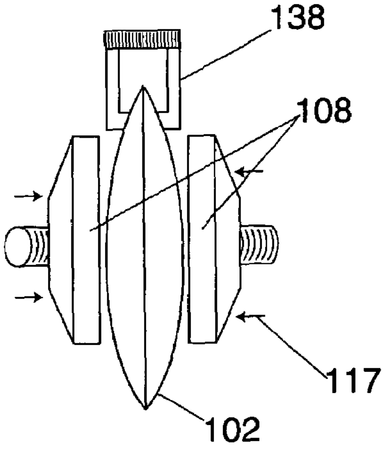
FIG. 9A depicts side view of FIG. 9.

In an alternative embodiment as shown in FIG. 9, instead of using the probe, a socket or lips device 138 could gently fit against the envelope corner. Blow the air or gas 139 into the envelope via the socket device's hollow channel 140. As in the above procedures, check the inflation as in FIG. 9A and then deflate the envelope by the side clamps as in FIG. 8A. As the side clamps compress against the envelope, use vacuum tube opening 141 attached to the wall of the airtight box and collect the airborne particles sample. Once collected, implement the same hazard detection and alert method, described above in operation 10 and 11.

Another way to check for successful the airflow injection is illustrated in FIG. 9; airflow meter 142 measures the flow of residual airflow 139A. The residual flow rate and amount should diminish when some airflow penetrate inside the envelope. Also, the injected airflow should cause backward pressure 143 on the top and bottom clamps.

Figure 10:
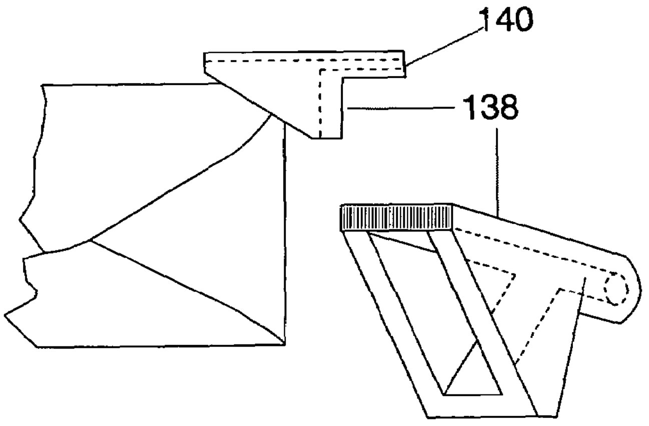
FIG. 10 shows the above socket/lips like device in detail.

FIG. 10 shows a socket or lips device 138 in detail. It's called a socket or lips device because the device's two front walls sandwich an envelope corner with opening 101 in the middle like a socket or lips would hold on to an item by grasping two opposite walls on the target item.

Additionally, the particle sample can be collected into a sealed container by this device for further testing. Alternatively, the whole airtight box may be removed and sent into the lab for further testing.

Problems could arise from probing underneath the envelope. This may be against the law for the US post office; however, addressee should not have a problem. Addressee can even open the envelope fully by incision and fully test the contents. So, a pair of scissors or a cutting device could be used to either partially or fully create an incision to affect the particle test.

Alternatively, to avoid probing underneath the flap, the air can be simply pumped out utilizing a hole with a vacuum hose attached 141 on the wall of the box by squeezing the existing air pockets already in the envelope with the side clamp without inflating it or the envelope sidewalls could be pulled apart to let the air in through the gap by grasping on the envelope sidewalls using vacuum suction or light adhesive on the side compressor clamp 108 on the envelope side walls. This action creates air inflow to the envelope, just as air is drawn into an accordion by pulling its side apart. Additionally, forced gas 133 into the envelope interior can be a toxin to kill any hazardous particles that might be inside the envelope.

In summary, from the description above, a number of advantages of my biochemical tester and method become evident. The operation is quick and simple, the operation can be assured of success by checking the package inflation or flow rate of the air, and the operation provides the capability to vent contagions from the package or used to deliver toxins to kill the contaminant particles without unsealing the package.

Accordingly, the reader will see that the biochemical tester and accompanying method of this invention can detect the presence of possible hazardous materials and illegal contraband in a shipping container simply, easily, safely, and assuredly.

Furthermore, the testing apparatus and method has the additional advantages by providing quick alert against both real or false hazardous particles, providing effective detection not only against biological, but chemical contrabands, such as poison, bombs, and illegal drugs, allowing preservation of the evidence for prosecution, providing a verification method of successful operation via inflation of the package or measured airflow change, allowing testing of the vast majority of shipment or mail packages, including most envelopes, express mail packages, envelopes with forwarding address hole opening, many box packaging, and the like, providing-an adaptable platform to launch future improved analytic devices and approaches, allowing safe operation in detection only mode by using only air in a preferred embodiment rather than using toxins or irradiation, allowing a much more effective and assured way to kill certain biological hazards via the verification process described above, if a toxin is used rather than just air and; allowing testing of packages in it original semi-sealed state.

Although the description above contains much specificity, these should not be construed as limiting the scope of the invention but as merely providing illustrations of some of the presently preferred embodiments of this invention.

For example, rather than checking for inflation of a package, which may have stiff and rigid walls, the slower flow rate and volume of air or pressure exerted on holding clamps can be used to check for infiltration of gas inside a package.

Thus, the scope of the invention should be determined by the appended claims and their legal equivalents, rather than by the example given.

I claim:

1. A method for detecting a specific content in an envelope comprising the steps of:

positioning said envelope proximal to an airflow device;

generating air movement internal to said envelope via at least one of a group consisting of a stream of air, a stream of gas, said airflow device, and one or more supplemental airflow devices;

collecting a sample of air via said airflow device;

transmitting said sample via said airflow device to at least one gathering device; and analyzing said sample to determine whether said content is present in said sample.

2. A method for detecting a specific content in an envelope comprising the steps of:

positioning said envelope proximal to an airflow device;

collecting a sample of air via said airflow device;

transmitting said sample via said airflow device to at least one gathering device; and analyzing said sample to determine whether said content is present in said sample;

wherein said collecting includes supplying one of a group consisting of air and gas to said envelope via at least one of a group consisting of a stream of air, a stream of gas, said airflow device, and one or more supplemental airflow devices.

3. A method for detecting a specific content in an envelope comprising the steps of:

altering an external dimension of said envelope;

positioning said envelope proximal to an airflow device;

collecting a sample of air via said airflow device;

transmitting said sample via said airflow device to at least one gathering device; and analyzing said sample to determine whether said content is present in said sample;

wherein said altering is performed with at least one of a group consisting of a clamp and a clip.

4. A method for detecting a specific content in an envelope comprising the steps of:

pulling at least one wall of said envelope away from an inner point of said envelope;

positioning said envelope proximal to an airflow device;

collecting a sample of air via said airflow device;

transmitting said sample via said airflow device to at least one gathering device; and analyzing said sample to determine whether said content is present in said sample.

5. A method for detecting a specific content in an envelope comprising the steps of:

positioning said envelope proximal to an airflow device;

inserting a probe coupled to an airflow device through a gap in said envelope;

collecting a sample of air via said airflow device;

transmitting said sample via said airflow device to at least one gathering device; and analyzing said sample to determine whether said content is present in said sample.

6. A method for detecting a specific content in an envelope comprising the steps of:

positioning said envelope proximal to an airflow device;

analyzing pressurization of said envelope;

collecting a sample of air via said airflow device;

transmitting said sample via said airflow device to at least one gathering device; and analyzing said sample to determine whether said content is present in said sample.

7. A method for detecting a specific content in an envelope comprising the steps of:

positioning said envelope proximal to an airflow device;

analyzing a physical change in at least one external dimension of said envelope;

collecting a sample of air via said airflow device;

transmitting said sample via said airflow device to at least one gathering device; and analyzing said sample to determine whether said content is present in said sample.

8. A method for detecting a specific content in an envelope comprising the steps of:

creating an aperture through a surface of said envelope via at least one of a group consisting of a sharp object, a scissor, and a syringe;

inserting a probe coupled to an airflow device through said aperture;

collecting a sample of air through said probe via said airflow device;

transmitting said sample via said airflow device to at least one gathering device; and analyzing said sample to determine whether said content is present in said sample.

* * * * *